US006353142B1

United States Patent
Zirngiebl et al.

(10) Patent No.: US 6,353,142 B1
(45) Date of Patent: Mar. 5, 2002

(54) PROCESS FOR THE ADIABATIC PREPARATION OF 3,4-DICHLORONITROBENZENE

(75) Inventors: Eberhard Zirngiebl, Köln; Bernd-Michael König, Gladbach; Hans-Martin Weber, Leverkusen; Thomas Linn, Grevenbroich; Hans-Joachim Raatz, Leverkusen, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/704,876

(22) Filed: Nov. 2, 2000

(30) Foreign Application Priority Data

Nov. 9, 1999 (DE) .......................... 199 53 722

(51) Int. Cl.$^7$ ............................................. C07C 205/06
(52) U.S. Cl. ....................................................... 568/938
(58) Field of Search ........................................... 568/938

(56) References Cited

U.S. PATENT DOCUMENTS

| 2,256,999 | A | 9/1941 | Castner ....................... 260/645 |
| 4,021,498 | A | 5/1977 | Alexanderson et al. ..... 260/645 |
| 4,453,027 | A | 6/1984 | Vaidyanathan ............... 568/937 |
| 5,648,565 | A | 7/1997 | Konig et al. ................. 568/940 |
| 5,714,647 | A | 2/1998 | Blank et al. ................. 568/937 |

OTHER PUBLICATIONS

Ullmann's Encyclopedia of Industrial Chemistry, 5$^{th}$ edition, vol. A 17, Editors, Barbara Elvers, Stephen Hawkins, Gail Schulz (month unavailable) 1991, p. 430, Nitro Compounds, Aromatic.

*Primary Examiner*—Brian J. Davis
(74) *Attorney, Agent, or Firm*—Joseph C. Gil; Richard E. L. Henderson; Diderico van Eyl

(57) ABSTRACT

1,2-Dichlorobenzene can be reacted very selectively under adiabatic reaction conditions to give 3,4-dichloronitrobenzene by intensively mixing 1,2-dichlorobenzene with nitric acid, sulphuric acid and water, simultaneously or successively, in their total amount, using a mixing energy of 1–50 watts per litre of the total reaction mixture, preferably 3–30 W/l, and maintaining a temperature of from 0 to 60° C. during mixing.

2 Claims, No Drawings

PROCESS FOR THE ADIABATIC PREPARATION OF 3,4-DICHLORONITROBENZENE

FIELD OF THE INVENTION

The present invention relates to a process for the highly selective waste-acid-free preparation of 3,4-dichloronitrobenzene utilizing the heat of reaction.

BACKGROUND OF THE INVENTION 3,4-Dichloronitrobenzene is an important intermediate for the production of crop protection agents and dyes.

3,4-Dichloronitrobenzene is prepared industrially by isothermal nitration of 1,2-dichlorobenzene at temperatures between 40 and 70° C. (Ullmann's Encyclopedia of Industrial Chemistry, 5$^{th}$ Edition, Vol. A17, p. 430, 1991). In this procedure, large quantities of contaminated waste acid are obtained which have to be disposed of or worked up in a cost-intensive operation. A disadvantage of this process is that considerable heat of reaction has to be removed safely, which places high demands on the safety engineering to be implemented.

In order to avoid the production of waste acid, processes must be sought which comprise integrated sulphuric acid concentration operation with utilization of the heat of reaction. This necessitates a circulating acid in which byproducts may not accumulate.

The above-mentioned disadvantages can be circumvented by carrying out the nitration process adiabatically. Adiabatic mononitration has already been described for various aromatic compounds.

In adiabatic nitration processes, the heat of reaction produced does not constantly have to be removed reliably by expensive cooling but, as intended, remains in the reaction system. Thus, the above-mentioned energetic and safety disadvantages in the isothermal nitration of 1,2-dichlorobenzene do not occur.

The heat of reaction can be utilized for heating the circulating sulphuric acid and for facilitating the reconcentration of the acid.

A further advantage of carrying out the reaction adiabatically is that the reaction rate is high: the reactions have ended after considerably less than 10 minutes. Moreover, it is possible to use cost-effective weak acid (HNO$_3$ about 60–65% strength).

EP 668 263 A1 describes a process for the adiabatic production of mononitrotoluenes. A mixture of toluene, nitric acid, sulphuric acid and water is reacted under adiabatic reaction conditions, the reaction components being mixed intensively and the temperature during mixing being between 20 and 110° C. The adiabatic mononitration of 1,2-dichlorobenzene is likewise already known.

An adiabatic nitration process for the preparation of mononitrohalogenobenzenes is claimed in U.S. Pat. No. 4,453,027. The conditions described therein, however, are unsuitable for an efficient industrial preparation of 3,4-dichloronitrobenzene. The nitrating acid used contains 11.2% by weight of HNO$_3$, 68.5% by weight of H$_2$SO$_4$ and 20.3% by weight of H$_2$O. In the case of adiabatic implementation, the high HNO$_3$ content leads to a temperature increase during the reaction of about 100° C., so that, at the end of the reaction, the temperature is considerably higher than 100° C., even if the reaction components are mixed, for example, at a temperature of as low as 45° C. As a consequence, in the production of 3,4-dichloronitrobenzene from 1,2-dichlorobenzene, higher amounts of the undesirable byproduct 2,3-dichloronitrobenzene are formed.

EP 675 104 A1 discloses a process for the adiabatic mononitration of mononitrohalogenobenzenes, and the nitration of 1,2-dichlorobenzene is mentioned explicitly. The adiabatic nitration is carried out by mixing the reaction components intensively, the temperature during mixing being between 60 and 160° C. and the temperature at the end of the reaction not exceeding 180° C. By this process, 1,2-dichlorobenzene can be converted into 3,4-dichloronitrobenzene. However, more than 16% by weight (based on the total amount of dichloronitrobenzenes) of the undesirable byproduct 2,3-dichloronitrobenzene are formed, which, in many cases, has to be disposed of at high cost or to be sold without covering the costs.

Accordingly, there has been a need for a process which combines the safety and economical advantages with respect to feed materials and the energy utilizable of an adiabatic process with a high selectivity for the formation of 3,4-dichloro-nitrobenzene.

We have now found reaction conditions at which the conflicting demands of a low formation of byproducts (2,3-dichloronitrobenzene and dinitrodichlorobenzenes) in combination with the high reaction rate required for carrying out the reaction adiabatically can be realized.

SUMMARY OF THE INVENTION

The invention relates to a process for preparing 3,4-dichloro-nitrobenzene by reacting 1,2-dichlorobenzene with an HNO$_3$/H$_2$SO$_4$/H$_2$O mixture with formation, essentially, of the dichloronitrobenzene and water of reaction. The process comprises the steps of (a) feeding the reactants 1,2-dichlorobenzene, HNO$_3$, H$_2$SO$_4$ and H$_2$O, in any sequence, into a reactor equipped with mixing elements, where
  (a1) the quantity of HNO$_3$ is from 1 to 5% by weight, the quantity of H$_2$SO$_4$ is from 70 to 92% by weight and the quantity of H$_2$O is the remainder to 100% by weight, and 100% by weight represents the sum of HNO$_3$+H$_2$SO$_4$+H$_2$O,
  (a2) the H$_2$O is employed as such, as dilution H$_2$O of the HNO$_3$, as dilution H$_2$O of the H$_2$SO$_4$ or in a plurality of the forms mentioned, and
  (a3) the molar ratio of 1,2-dichlorobenzene to HNO$_3$ is from 0.9 to 1.5;

(b) rapidly and intensively mixing the total quantity of the reactants, for which a mixing energy of from 1 to 50 watts per litre of the overall mixture, preferably from 3 to 30 W/l, is employed, (c) carrying out the reaction under adiabatic conditions, the reactants being fed in at temperatures such that the mixing takes place in the range from 0 to 60° C. and the temperature at the end of the reaction does not exceed 100° C., (d) separating the reaction mixture, after carrying out the reaction, into an organic and an inorganic phase, and (e) working up the substantially HNO$_3$-free inorganic phase by distillation with removal of water.

These and other features, aspects, and advantages of the present invention will become better understood with reference to the following description and appended claims.

DESCRIPTION OF THE INVENTION

The process according to the invention can be carried out continuously or batchwise, preferably continuously.

The continuous procedure can be carried out, for example, as follows. The total quantity of the reactants is rapidly mixed with the aid of mixing elements and is fed as a mixture into a reactor. The mixing time for the continuous procedure is generally less than 3 seconds, for example, from 1 msec to 2.99 sec, preferably from 1 msec to 2 sec. The reactor is insulated, if desired, and substantially prevents back-mixing and is operated adiabatically. For the substantial prevention of back-mixing, the reactor is subdivided or is composed of a plurality of chambers or units; at the transitions between the reactor parts, the reaction mixture is redispersed. After full reaction, the mixture flows out and is separated in a separation vessel; the separation occurs rapidly. The organic phase is worked up in the usual manner, for example, by washing and distillation, or is fed immediately to a second nitration. In general, especially when there is an excess of 1,2-dichlorobenzene, the inorganic phase separated off is virtually free of nitric acid. Should this not be the case, especially when there is an excess of nitric acid, residual nitric acid can be consumed in a downstream reactor with addition of further 1,2-dichlorobenzene in the manner of a reactive extraction. The inorganic acid phase, substantially freed of nitric acid, is preferably fed to a flash evaporation with utilization of the heat of reaction absorbed and under reduced pressure. In this operation, water is removed from the acid and the acid is preferably and simultaneously brought to the initial concentration for step a). This recycling of the worked-up inorganic phase ($H_2SO_4$, $H_2O$) to the process results in a circulation procedure for the $H_2SO_4$; it may be expedient to expel a small proportion of this $H_2SO_4$ in order to reduce any contamination to a low level. In the event that the inorganic phase still contains 1,2-dichlorobenzene, dichloronitrobenzenes and any organic byproducts, it may be expedient to strip the inorganic phase prior to the flash evaporation in order to remove the organic components. The water obtained subsequently as flash condensate is then of relatively high purity, and is easier to dispose of. Of course, the flash condensate can also be freed from organic components by stripping, to leave, similarly, a residual flash condensate of relatively high purity. The organic components obtained in the downstream reaction of the $HNO_3$ with further 1,2-dichlorobenzene and in the stripping operation or during reconcentration of the substantially $HNO_3$-free inorganic phase can be added to the process at a suitable point (1,2-dichlorobenzene, dichloro (di)nitrobenzene) or are expelled and disposed of (contaminants, byproducts).

The reactants can be fed together or else individually or as mixtures of two or three thereof, simultaneously or in succession, to the reactor equipped with mixing elements. The feedstocks can be mixed, for example, in such a way that 1,2-dichlorobenzene and nitric acid are added to the reconcentrated, spent sulphuric acid, simultaneously or in succession, as two separate streams, in which case, the nitric acid may be diluted by water and/or sulphuric acid and water. The 1,2-dichlorobenzene can also be premixed with water and sulphuric acid and the resulting emulsion can be mixed further, rapidly and intensively, with nitric acid, which may be mixed with sulphuric acid and/or water. Furthermore, the 1,2-dichlorobenzene can also be intensively mixed with a mixed acid comprising $H_2SO_4$, $HNO_3$ and $H_2O$. Those skilled in the art will be readily able to detect still more variants for feeding the reactants, for their intensive mixing and for the subsequent treatment according to the invention. The mixing elements known in the art are suitable for this purpose, for example: (1) static mixers, (2) pumps, (3) nozzles, (4) agitators or combinations thereof.

The sequence and combination of mixing the reactants nitric acid and 1,2-dichlorobenzene and also sulphuric acid and water with one another is of little importance for the success of the reaction, provided the reaction mixture has the composition according to the invention after the overall mixing, and the mixing takes place at the intensity according to the invention.

The feeding and intensive mixing of the reactants are followed, in the continuous procedure, by at least two dispersion operations. For this purpose, the reactor contains perforated metal sheets, slotted metal sheets, impact baffles, agitators or similar internals and/or elements which are known for this purpose to those skilled in the art.

Continuously operated reactors for the purpose according to the invention, which may be mentioned by way of example, include (i) tubular reactors having internals for redispersion, such as flow breakers, deflection baffles, static mixers, agitators and the like; (ii) vigorously stirred reactors in cascade arrangement; (iii) loop reactors having internals as above; (iv) combinations of a plurality of the apparatus mentioned; (v) other reactors of equivalent action, such as chamber reactors with agitators in each chamber. Tubular reactors having internals are preferably employed. The internals are preferably perforated metal sheets. All internals represent subdivisions of the overall apparatus, which serve equally for the redispersion and for the substantial prevention of back-mixing.

After the intensive mixing, after each dispersion and after the mixture has flowed through a certain part-length of the reactor, coalescence of the dispersion droplets is observed, which can be reversed by redispersion. The number of dispersion operations is, according to the invention, 2–50, preferably 3–30, particularly preferably 4–20. In order to overcome the pressure losses which occur in these operations, a mixing energy, per litre of the overall reaction mixture, of 1–50 Watts/litre, preferably 3–30 W/l, is input into the reaction system with the reactants.

The reactants are mixed in the range from 0 to 60° C., preferably from 10 to 50° C. and particularly preferably from 20 to 40° C. Adiabatic reaction conditions are maintained. The final temperature depends on the value of the mixing temperature, on the proportion of the reactants and on the conversion; it does not exceed 100° C. in general, preferably not 85° C. and particularly preferably not 70° C.

The content of added nitric acid in the reaction mixture at the time of mixing, relative to the sum of nitric acid, sulphuric acid and water, is from 1 to 5% by weight, preferably from 1 to 4% by weight and particularly preferably from 1.5 to 3% by weight. Nitric acid can be used in highly concentrated form or in azeotropically boiling form, for example, as 60–98% by weight strength $HNO_3$, but preferably in the form of the cheaply available "weak acid", having a strength of about 60–65% by weight.

The content of sulphuric acid in the reaction mixture at the time of mixing, relative to the sum of nitric acid, sulphuric acid and water, is from 70 to 92% by weight, preferably from 80 to 90% by weight and particularly preferably from 82 to 88% by weight.

The remainder to 100% by weight is $H_2O$. This can be employed as such, as dilution $H_2O$ of the $H_2SO_4$, as dilution $H_2O$ of the $HNO_3$ or in a plurality of the forms mentioned. In its preferred form, $H_2O$ is present as dilution $H_2O$ of both the $H_2SO_4$ and the $HNO_3$.

The molar ratio of 1,2-dichlorobenzene to $HNO_3$ is generally from 0.9 to 1.5. To minimize the formation of undesirable dinitrohalogeno-benzenes, the molar ratio of halogenobenzene to nitric acid is preferably from 1.0 to 1.5, particularly preferably from 1.01 to 1.3 and very particularly preferably from 1.05 to 1.2.

1,2-Dichlorobenzene and $HNO_3$ are introduced into the process and dichloronitrobenzene and $H_2O$ are ejected, while the $H_2SO_4/H_2O$ mixture described represents the reaction medium. Since, when the process is carried out industrially, dilute nitric acids are advantageously used, additionally to the water of reaction, dilution $H_2O$ of the $HNO_3$ must also be ejected.

The organic phase arising in the separation of the reaction mixture can be worked up to give pure 3,4-dichloronitrobenzene or be fed to the second nitration. In the former case, at least molar amounts of 1,2-dichlorobenzene or a slight molar excess is used, as described above, in order not only to consume the $HNO_3$ but also to repress the second nitration; any 1,2-dichlorobenzene excess is distilled off from the organic phase. Before this, the organic phase can be washed in order to remove water-, acid-or alkali-soluble impurities, such as inorganic and organic acids and phenolic impurities. The formation of oxidation products (phenol compounds) is strongly suppressed. Likewise, the formation of dinitrodichlorobenzenes is highly repressed. However, these dinitrodichlorobenzenes are not an interference if a second nitration is in any case intended; therefore, in such cases, the procedure may also be carried out with a slight 1,2-dichlorobenzene deficiency.

As a model for a back-mixing-free industrial reactor, and to represent the batchwise procedure, a batch formulation in a vigorously stirred, heat-insulated stirred flask, e.g., in a so-called sulphonation beaker, which is furnished with baffles, can serve in the laboratory. In this case, 1,2-dichlorobenzene, sulphuric acid and water are initially charged, for example, at 30° C., and nitric acid, which is heated to the feed temperature according to the invention and which can be diluted by water and/or sulphuric acid, is added in the course of a few seconds. After the metered addition, the reaction is allowed to proceed adiabatically. The final temperature is reached after about 0.5 to 10 minutes. Alternatively, it is also possible to initially charge the total amount of $HNO_3$, $H_2SO_4$ and $H_2O$ and to add 1,2-dichlorobenzene to this mixture; other dosage variants will be readily recognized by the person skilled in the art. The content of the reaction vessel corresponds in this case in the course of time to a part-volume in the axial movement to a tubular reactor with plug flow. That which occurs successively in time in the batch formulation proceeds successively with respect to position in, for example, a tubular reactor.

After the reaction temperature has been achieved, the agitator is halted. The phases separate in at most 10 minutes. A continuous industrial reactor is preferably dimensioned in such a way that the reaction mixture reaches the final reaction temperature in the reactor.

The acid phase, which is separated off after the reaction, at least at the level of the final reaction temperature in question, is reconcentrated in the manner described above, it being possible to insert the reactive extraction or extraction described above. After the process according to the invention, the circulating acid, which is circulated in this manner, contains, for example, less than 0.2% by weight of nitric acid and less than 0.5% by weight of nitrous acid, and, if appropriate, small amounts of organic impurities.

The process according to the invention is distinguished by the fact that the undesirable byproduct 2,3-dichloronitrobenzene is formed in considerably lower amounts than by the known processes. If, according to the invention, the reaction partners in the adiabatic nitration of 1,2-dichlorobenzene are mixed at 30° C., the amount of $HNO_3$ used being 3.0% by weight, based on the amount of water, nitric acid and sulphuric acid employed, 12.2% by weight (based on the sum of the dichloromononitrobenzenes formed) of the undesirable byproduct 2,3-dichloronitrobenzene are formed. If, however, the reactants are mixed according to Example 2 from EP 675 104 A1 at 110° C., the amount of $HNO_3$ used being unchanged at 3.0% by weight, 16.3% by weight of 2,3-dichloro-nitrobenzene are formed. Thus, using the process according to the invention, almost 25% less of the undesirable byproduct are formed. In addition to the temperature of the reactants during mixing, the amount of $HNO_3$ employed is likewise of decisive importance for the process according to the invention. An increasing content of $HNO_3$ in the mixed acid used results in a higher temperature increase during the adiabatic nitration which, in turn, leads to an increased formation of byproducts. In the present Example 2 (1.5% by weight of $HNO_3$), 11.5% by weight of the undesirable 2,3-dichloronitrobenzene are formed, in the present Example 1 (3.0% by weight of $HNO_3$), 12.2% by weight are formed. If a mixed acid with an $HNO_3$ content of more than 5% by weight is used, considerably more undesirable byproduct is formed.

Using the examples below, the process according to the invention is illustrated in more detail. However, these examples do not represent any limitation of the spirit of the invention.

EXAMPLES

Example 1

In a continuously operated unit, a stream of 188.0 kg of $H_2SO_4$ (87% by weight) per hour was mixed with a stream of 9.56 kg of $HNO_3$ (62% by weight) per hour. The resulting mixed acid contained 3.0% by weight of $HNO_3$. The mixed acid was, at the inlet of a tubular reactor, mixed with a stream of 15.21 kg of 1,2-dichlorobenzene per hour. The temperature at the point of mixing was 30° C. The reaction mixture left the tubular reactor after 3 minutes, having a temperature of 67° C. The organic and the inorganic phase of the reaction mixture were then separated from one another in a phase separator.

This gave:

18.60 kg/h of organic phase

Composition (calibrated GC):

| | |
|---|---|
| 1,2-Dichlorobenzene: | 7.9% by weight |
| 3,4-Dichloronitrobenzene: | 80.5% by weight |
| 2,3-Dichloronitrobenzene: | 11.5% by weight |
| Dinitrodichlorobenzenes: | 0.03% by weight |

The acid phase contained 0.84 kg/h of 3,4-dichloronitrobenzene and 0.07 kg/h of 2,3-dichloronitrobenzene.

Thus, the total proportion of 2,3-dichloronitrobenzene, based on the sum of the di-chloromononitrobenzenes formed, was 12.2% by weight.

Example 2

In a continuously operated unit, a stream of 188.0 kg of $H_2SO_4$ (88% by weight) per hour was mixed with a stream of 4.66 kg of $HNO_3$ (62% by weight) per hour. The resulting mixed acid contained 1.5% by weight of $HNO_3$. The mixed acid was, at the inlet of a tubular reactor, mixed with a stream of 6.74 kg of 1,2-dichlorobenzene per hour. The temperature at the point of mixing was 30° C. The reaction mixture left the tubular reactor after 3 minutes, having a temperature of 48° C.

This gave after phase separation:

7.20 kg/h of organic phase

Composition (calibrated GC):

| | |
|---|---|
| 1,2-Dichlorobenzene: | 3.6% by weight |
| 3,4-Dichloronitrobenzene: | 84.4% by weight |
| 2,3-Dichloronitrobenzene: | 11.9% by weight |
| Dinitrodichlorobenzenes: | 0.08% by weight |

The acid phase contained 1.48 kg/h of 3,4-dichloronitrobenzene and 0.13 kg/h of 2,3-dichloronitrobenzene.

Thus, the total proportion of 2,3-dichloronitrobenzene, based on the sum of the di-chloromononitrobenzenes formed, was 11.5% by weight.

Example 3

In a continuously operated unit, a stream of 141.0 kg of $H_2SO_4$ (86.6% by weight) per hour was mixed with a stream of 5.31 kg of $HNO_3$ (62% by weight) per hour. The resulting mixed acid contained 2.25% by weight of $HNO_3$. The mixed acid was, at the inlet of a tubular reactor, mixed with a stream of 8.45 kg of 1,2-dichlorobenzene per hour. The temperature at the point of mixing was 30° C. The reaction mixture left the tubular reactor after 3 minutes, having a temperature of 57° C.

This gave after phase separation:

10.04 kg/h of organic phase

Composition (calibrated GC):

| | |
|---|---|
| 1,2-Dichlorobenzene: | 8.4% by weight |
| 3,4-Dichloronitrobenzene: | 80.4% by weight |
| 2,3-Dichloronitrobenzene: | 11.2% by weight |
| Dinitrodichlorobenzenes: | 0.04% by weight |

The acid phase contained 0.75 kg/h of 3,4-dichloronitrobenzene and 0.06 kg/h of 2,3-dichloronitrobenzene.

Thus, the total proportion of 2,3-dichloronitrobenzene, based on the sum of the dichloromononitrobenzenes formed, was 11.8% by weight.

Example 4

In a heat-insulated sulphonation beaker (diameter 100 mm), furnished with baffles and two turbine agitators (diameter 39.9 mm) seated on a shaft, 667.8 g of $H_2SO_4$ (86.6% strength) and 32.3 g (0.333 mol) of $HNO_3$ (65% strength) were initially charged at 30° C. with stirring (using a specific agitator power of 22 W/l), and this mixture was then, in the course of 3 seconds, admixed with 49.0 g (0.333 mol) of 1,2-dichlorobenzene having a temperature of 30° C., and the mixture was allowed to react without cooling. After 170 seconds, the reaction mixture had reached the final temperature of 67° C. and the agitator was halted. Phase separation gave 58.3 g of organic phase.

| | |
|---|---|
| 1,2-Dichlorobenzene: | 1.2% by weight |
| 3,4-Dichloronitrobenzene: | 86.4% by weight |
| 2,3-Dichloronitrobenzene: | 12.3% by weight |
| Dinitrodichlorobenzenes: | 0.03% by weight |

From the acid phase, 4.70 g of 3,4-dichloronitrobenzene and 0.49 g of 2,3-dichloronitrobenzene could be isolated.

Thus, the total proportion of 2,3-dichloronitrobenzene, based on the sum of the dichloromononitrobenzenes formed, was 12.2% by weight.

Although the present invention has been described in detail with reference to certain preferred versions thereof, other variations are possible. Therefore, the spirit and scope of the appended claims should not be limited to the description of the versions contained therein.

What is claimed is:

1. A process for preparing 3,4-dichloronitrobenzene by reacting 1,2-dichlorobenzene with an $HNO_3/H_2SO_4/H_2O$ mixture with formation of dichloronitrobenzene and water of reaction, wherein the process comprises (a) feeding the reactants 1,2-dichlorobenzene, $HNO_3$, $H_2SO_4$ and $H_2O$ in any sequence into a reactor equipped with mixing elements, in which (a1) the quantity of $HNO_3$ is from 1 to 5% by weight, the quantity of $H_2SO_4$ is from 70 to 92% by weight and the quantity of $H_2O$ is the remainder to 100% by weight, and 100% by weight represent the sum of $HNO_3+H_2SO_4+H_2O$;

(a2) the $H_2O$ is employed as such, as dilution $H_2O$ of the $HNO_3$, as dilution $H_2O$ of the $H_2SO_4$ or in a plurality of the forms mentioned; and (a3) the molar ratio of 1,2-dichlorobenzene to $HNO_3$ is from 0.9 to 1.5, (b) rapidly and intensively mixing the total quantity of the reactants, for which a mixing energy of from 1 to 50 watts per litre of the overall mixture is employed, (c) carrying out the reaction under adiabatic conditions, the reactants being fed in at temperatures such that the mixing takes place at a temperature of from 0 to about 50° C., and the temperature at the end of the reaction does not exceed 100° C., (d) separating the reaction mixture, after carrying out the reaction, into an organic and an inorganic phase, and (e) working up the substantially $HNO_3$-free inorganic phase by distillation with removal of water.

2. The process of claim 1, wherein the reactants being fed in at temperatures such that the mixing takes place at a temperature of from about 10 to about 50° C.

* * * * *